(12) United States Patent
Broughton et al.

(10) Patent No.: US 6,337,331 B1
(45) Date of Patent: Jan. 8, 2002

(54) TRIAZOLO-PYRIMIDINE AS LIGANDS FOR GABA RECEPTORS

(75) Inventors: Howard Barff Broughton; Jose Luis Castro Pineiro, both of Bishop's Stortford; Ian James Collins, Ware; Karl Richard Gibson, Bishop's Stortford; Michael Rowley, Chelmsford; Leslie Joseph Street, Little Hallingbury, all of (GB)

(73) Assignee: Merck Sharp & Dohme Ltd., Hoddesdon (GB)

( * ) Notice: Subject to any disclaimer, the term of this patent is extended or adjusted under 35 U.S.C. 154(b) by 0 days.

(21) Appl. No.: 09/700,003

(22) PCT Filed: Jun. 9, 1999

(86) PCT No.: PCT/GB99/01827

§ 371 Date: Nov. 8, 2000

§ 102(e) Date: Nov. 8, 2000

(87) PCT Pub. No.: WO99/65907

PCT Pub. Date: Dec. 23, 1999

(30) Foreign Application Priority Data

Jun. 16, 1998 (GB) .............................. 9813006

(51) Int. Cl.$^7$ .................... A61K 31/505; C07D 491/00; C07D 239/00; C07D 487/00
(52) U.S. Cl. ................ 514/257; 514/258; 514/267; 544/247; 544/251; 544/252; 544/263
(58) Field of Search .................... 514/257, 258, 514/267; 544/247, 251, 252, 263

(56) References Cited

U.S. PATENT DOCUMENTS

| | | | |
|---|---|---|---|
| 5,231,094 A | * 7/1993 | Bru-Magniez et al. ... | 514/223.2 |
| 5,677,309 A | 10/1997 | Chen et al. ................ | 514/267 |
| 5,854,237 A | * 12/1998 | Albright et al. ............ | 514/220 |
| 6,124,289 A | * 9/2000 | He et al. .................... | 514/245 |

FOREIGN PATENT DOCUMENTS

WO    WO 98/04559    2/1998

OTHER PUBLICATIONS

Biagi et al., II Farmaco, 51: 131–136 (1996).
Bruno et al., II Farmaco, 51: 137–140 (1996).
Wafford et al., Mol. Pharmacol., 50:670–678 (1996).
Dawson et al., Psychopharmacology, 121: 109–117 (1995).
Bayley et al., J. Psychopharmacology, 10: 206–213 (1996).
Bristow et al., J. Pharmacology, Exp. Ther., 279: 492–501 (1996).

* cited by examiner

Primary Examiner—Mukunk J. Shah
Assistant Examiner—Tamthom N. Truong
(74) Attorney, Agent, or Firm—Shu L. Lee; David L. Rose

(57) ABSTRACT

Substituted or 6,7-ring fused 1,2,3-triazolo[1,5-α]-pyrimidine derivatives are selective ligands for $GABA_A$ receptors useful in the treatment of disorders of the central nervous system, including anxiety and convulsions.

10 Claims, No Drawings

TRIAZOLO-PYRIMIDINE AS LIGANDS FOR GABA RECEPTORS

This is an application under 35 U.S.C. 371 of PCT/GB99/01827 and claims priority from Great Britain Application No. 9813006.5, filed Jun. 16, 1998.

BACKGROUND

The present invention relates to a class of substituted triazolo-pyrimidine derivatives and to their use in therapy. More particularly, this invention is concerned with substituted 1,2,3-triazolo[1,5-a]pyrimidine derivatives which are ligands for $GABA_A$ receptors and are therefore useful in the therapy of deleterious mental states.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six $\alpha$ subunits, four $\beta$ subunits, three $\gamma$ subunits, one $\delta$ subunit, one $\epsilon$ subunit and two $\rho$ subunits.

Although knowledge of the diversity of the $GABA_A$ receptor gene family represents a huge step forward in our understanding of this ligand-gated ion channel, insight into the extent of subtype diversity is still at an early stage. It has been indicated that an $\alpha$ subunit, a $\beta$ subunit and a $\gamma$ subunit constitute the minimum requirement for forming a fully functional $GABA_A$ receptor expressed by transiently transfecting cDNAs into cells. As indicated above, $\delta$, $\epsilon$ and $\rho$ subunits also exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one $\alpha$, one $\beta$ and one $\gamma$ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, $\alpha 1\beta 2\gamma 2$, $\alpha 2\beta 2/3\gamma 2$, $\alpha 3\beta \gamma 2/3$, $\alpha 2\beta \gamma 1$, $\alpha 5\beta 3\gamma 2/3$, $\alpha 6\beta \gamma 2$, $\alpha 6\beta \delta$ and $\alpha 4\beta \delta$. Subtype assemblies containing an $\alpha 1$ subunit are present in most areas of the brain and are thought to account for over 40% of $GABA_A$ receptors in the rat. Subtype assemblies containing $\alpha 2$ and $\alpha 3$ subunits respectively are thought to account for about 25% and 17% of $GABA_A$ receptors in the rat. Subtype assemblies containing an $\alpha 5$ subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the $\alpha$ subunit in combination with a $\beta 1$ subunit and $\gamma 2$. This is the most abundant $GABA_A$ receptor subtype, and is believed to represent almost half of all $GABA_A$ receptors in the brain.

Two other major populations are the $\alpha 2\beta\gamma 2$ and $\alpha 3\beta\gamma 2/3$ subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain $\alpha 5$-containing subtype assemblies. The physiological role of these subtypes has hitherto been unclear because no sufficiently selective agonists or antagonists were known.

It is now believed that agents acting as BZ agonists at $\alpha 1\beta\gamma 2$, $\alpha 2\beta\gamma 2$ or $\alpha 3\beta\gamma 2$ subunits will possess desirable anxiolytic properties. Compounds which are modulators of the benzodiazepine binding site of the $GABA_A$ receptor by acting as BZ agonists are referred to hereinafter as "$GABA_A$ receptor agonists". The $\alpha 1$-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the $\alpha 1$ subunit. Accordingly, it is considered that $GABA_A$ receptor agonists which interact more favourably with the $\alpha 2$ and/or $\alpha 3$ subunit than with $\alpha 1$ will be effective in the treatment of anxiety with a reduced propensity to cause sedation. Also, agents which are antagonists or inverse agonists at $\alpha 1$ might be employed to reverse sedation or hypnosis caused by $\alpha 1$ agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions: migraine: depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as post-operative nausea and vomiting; eating disorders including anorexia nervosa and bulimia nervosa; premenstrual syndrome; muscle spasm or spasticity, e.g. in paraplegic patients; and hearing loss. Selective ligands for $GABA_A$ receptors may also be effective as pre-medication prior to anaesthesia or minor procedures such as endoscopy, including gastric endoscopy.

WO 98/04559 describes a class of substituted and 7,8-ring fused 1,2,4-triazolo[4,3-b]pyridazine derivatives which are stated to be selective ligands for $GABA_A$ receptors beneficial in the treatment and/or prevention of neurological disorders including anxiety and convulsions. There is in that publication, however, no disclosure nor any suggestion that the central triazolo-pyridazine ring system can be replaced by any other ring system. In particular, there is no disclosure nor any suggestion in that publication that the specified triazolo-pyridazine ring system can be replaced by a 1,2,3-triazolo[1,5-α]pyrimidine ring system.

Biagi et al., in Il Farmiaco, 1996, 51, 137–140, describe the synthesis of iiLter alia 3-phenyl-5-methoxy-1,2,3-triazolo[1,5-α]quinazoline, which is stated therein to be a benzodiazepine receptor partial agonist agent. There is, however, no disclosure nor any suggestion in that publication of replacing the methoxy substituent in the 5-position with an optionally substituted cycloalkyl-alkoxy, aryl-alkoxy or heteroaryl-alkoxy moiety.

SUMMARY OF THE INVENTION

The present invention is directed to a compound according to Formula (I) or a pharmaceutically acceptable salt thereof that is a $GABA_A$ ligand useful in the treatment of disorders of the central nervous system:

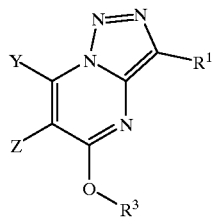

(I)

DETAILED DESCRIPTION OF THE INVENTION

The present invention provides a class of triazolo-pyrimidine derivatives which possess desirable binding properties at various $GABA_A$ receptor subtypes. The compounds in accordance with the present invention have good affinity as ligands for the α2 and/or α3 subunit of the human $GABA_A$ receptor. The compounds of this invention may interact more favourably with the α2 and/or α3 subunit than with the α1 subunit. Desirably, the compounds of the invention will exhibit functional selectivity in terms of a selective efficacy for the α2 and/or α3 subunit relative to the α1 subunit.

The compounds of the present invention are $GABA_A$ receptor subtype ligands having a binding affinity ($K_i$) for the α2 and/or α3 subunit, as measured in the assay described hereinbelow, of 100 nM or less, typically of 50 nM or less, and ideally of 10 nM or less. The compounds in accordance with this invention may possess at least a 2-fold, suitably at least a 5-fold, and advantageously at least a 10-fold, selective affinity for the α2 and/or α3 subunit relative to the α1 subunit. However, compounds which are not selective in terms of their binding affinity for the α2 and/or α3 subunit relative to the α1 subunit are also encompassed within the scope of the present invention; such compounds will desirably exhibit functional selectivity in terms of a selective efficacy for the α2 and/or α3 subunit relative to the α1 subunit.

The present invention provides a compound of formula I, or a salt or prodrug thereof:

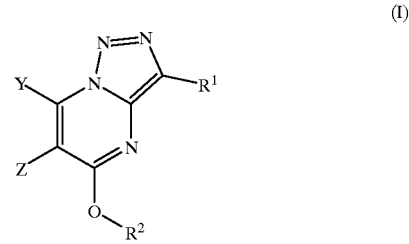

(I)

wherein

Y represents hydrogen or $C_{1-6}$ alkyl; and

Z represents $C_{1-6}$ alkyl, $C_{3-7}$ cycloalkyl, $C_{4-7}$ cycloalkenyl, $C_{6-8}$ bicycloalkyl, aryl, $C_{3-7}$ heterocycloalkyl, heteroaryl, $C_{2-7}$ alkoxycarbonyl or di($C_{1-6}$)alkylamino, any of which groups may be optionally substituted; or Y and Z are taken together with the two intervening carbon atoms to form a ring selected from $C_{5-9}$ cycloalkenyl, $C_{6-10}$ bicycloalkenyl, tetrahydropyridinyl, pyridinyl and phenyl, any of which rings may be optionally benzo-fused and/or substituted;

$R^1$ represents $C_{3-7}$ cycloalkyl, phenyl, furyl, thienyl or pyridinyl, any of which groups may be optionally substituted; and $R^2$ represents $C_{3-7}$ cycloalkyl($C_{1-6}$)alkyl, aryl($C_{1-6}$)alkyl or heteroaryl($C_{1-6}$)alkyl, any of which groups may be optionally substituted.

Where Y and Z are taken together with the two intervening carbon atoms to form a ring, the resulting compounds of formula I above incorporate the relevant cycloalkenyl, bicycloalkenyl, tetrahydropyridinyl, pyridinyl or phenyl ring fused to the central triazolo-pyridazine ring system as depicted in formula I.

Where Y and Z are taken together with the two intervening carbon atoms to form a $C_{5-9}$ cycloalkenyl ring, this ring may be a cyclopentenyl, cyclohexenyl, cycloheptenyl, cyclooctenyl or cyclononenyl ring, suitably cyclohexenyl or cycloheptenyl.

Where Y and Z are taken together with the two intervening carbon atoms to form a $C_{6-10}$ bicycloalkenyl ring, this ring may be a bicyclo[2.1.1]hex-2-enyl, bicyclo[2.2.1]hept-2-enyl, bicyclo[2.2.2]oct-2-enyl, bicyclo[3.2.2]non-6-enyl or bicyclo[3.3.2]dec-9-enyl ring, suitably bicyclo[2.2.1] hept-2-enyl, bicyclo[2.2.2]oct-2-enyl or bicyclo[3.2.2]non-6-enyl, and especially bicyclo[2.2.2]oct-2-enyl.

Where Y and Z are taken together with the two intervening carbon atoms to form a ring, this ring may be optionally benzo-fused. By way of illustration, Y and Z taken together with the two intervening carbon atoms may represent a benzo-fused cyclohexenyl ring, whereby the resulting ring is dihydronaphthyl.

The groups Y, Z, $R^1$ and $R^2$ may be unsubstituted, or substituted by one or more. suitably by one or two, substituents. In general, the groups Y, Z, $R^1$ and $R^2$ will be unsubstituted or monosubstituted. Examples of optional substituents on the groups Y, Z, $R^1$ and $R^2$ include $C_{1-6}$ alkyl, aryl($C_{1-6}$)alkyl, pyridyl($C_{1-6}$)alkyl, halogen, halo($C_{1-6}$) alkyl, cyano, cyano($C_{1-6}$)alkyl, hydroxy, hydroxymethyl, $C_{1-6}$ alkoxy, $C_{3-7}$ cycloalkyl($C_{1-6}$)alkoxy, $C_{3-7}$ cycloalkoxy, amino($C_{1-6}$)alkyl, di($C_{1-6}$)alkylamino($C_{1-6}$)alkyl, di($C_{1-6}$) alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl, di($C_{1-6}$)alkylmorpholinyl($C_{1-6}$)alkyl and imidazolyl($C_{1-6}$)alkyl. Representative substituents include $C_{1-6}$ alkyl, aryl($C_{1-6}$)alkyl, halogen, cyano, hydroxy, hydroxymethyl, $C_{1-6}$ alkoxy and $C_{3-7}$ cycloalkyl($C_{1-6}$)alkoxy. Particular substituents include methyl, ethyl and fluoro, especially methyl or fluoro.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl, tert-butyl and 1,1-dimethylpropyl. Derived expressions such as "$C_{1-6}$ alkoxy" are to be construed accordingly.

Typical $C_{3-7}$ cycloalkyl groups include cyclopropyl, cyclobutyl, cyclopentyl and cyclohexyl.

The expression "$C_{3-7}$ cycloalkyl($C_{1-6}$)alkyl" as used herein includes cyclopropylmethyl, cyclobutylmethyl, cyclopentylmethyl and cyclohexylmethyl.

Typical $C_{4-7}$ cycloalkenyl groups include cyclobutenyl, cyclopentenyl and cyclohexenyl.

Typical aryl groups include phenyl and naphthyl, preferably phenyl.

The expression "aryl($C_{1-6}$)alkyl" as used herein includes benzyl, phenylethyl, phenylpropyl and naphthylmethyl.

Suitable heterocycloalkyl groups include azetidinyl, pyrrolidinyl, piperidinyl, piperazinyl, morpholinyl and thiomorpholinyl groups.

Suitable heteroaryl groups include pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl. indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl.

The term "halogen" as used herein includes fluorine, chlorine, bromine and iodine, especially fluorine or chlorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Suitably, Y represents hydrogen or methyl, especially hydrogen.

Examples of suitable values for the substituent Z include methyl, ethyl, isopropyl, tert-butyl, 1,1-dimethylpropyl, methyl-cyclopropyl, cyclobutyl, methyl-cyclobutyl, cyclopentyl, methyl-cyclopentyl, cyclohexyl, cyclobutenyl, bicyclo[2.1.1]hex-1-yl, bicyclo[2.2.1]heptan-1-yl, phenyl, pyrrolidinyl, methyl-pyrrolidinyl, piperidinyl, morpholinyl, thiomorpholinyl, pyridinyl, furyl, thienyl, chloro-thienyl, methoxycarbonyl and diethylamino, especially cyclobutyl or phenyl.

In a particular embodiment, the substituent Z represents $C_{3-7}$ cycloalkyl, either unsubstituted or substituted by $C_{1-6}$ alkyl, especially methyl. Favourably, Z represents cyclobutyl.

When Y and Z are taken together with the two intervening carbon atoms to form a ring, representative compounds according to the invention include those of structure IA to IL:

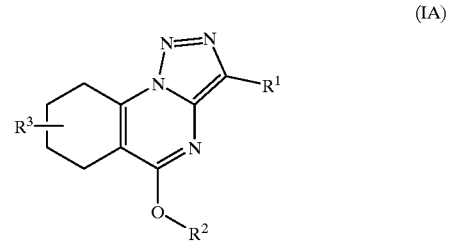

(IA)

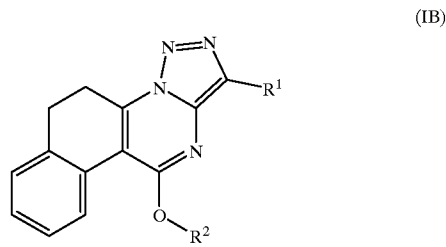

(IB)

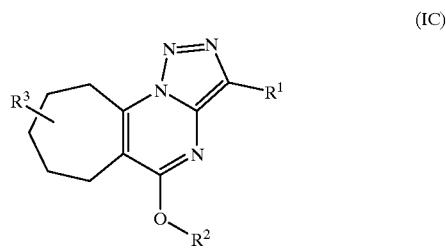

(IC)

wherein $R^1$ and $R^2$ are as defined above;
$R^3$ represents hydrogen, $C_{1-6}$ alkyl, aryl($C_{1-6}$)alkyl, halogen, cyano, hydroxy, hydroxymethyl or $C_{1-6}$ alkoxy; and
$R^4$ represents hydrogen or $C_{1-6}$ alkyl.

Suitably, $R^3$ represents hydrogen or $C_{1-6}$ alkyl, especially hydrogen or methyl.

Suitably, $R^4$ represents hydrogen or methyl.

Favoured triazolo-pyrimidine derivatives according to the present invention include the compounds represented by formula IL as depicted above.

Examples of typical optional substituents on the group $R^1$ include methyl, fluoro and methoxy.

Representative values of $R^1$ include cyclopropyl, phenyl, methylphenyl, fluorophenyl, difluorophenyl, methoxyphenyl, furyl, thienyl, methyl-thienyl and pyridinyl. More particularly, $R^1$ may represent unsubstituted or monosubstituted phenyl. Most particularly, $R^1$ represents phenyl or fluorophenyl.

Suitably, $R^2$ represents aryl($C_{1-6}$)alkyl or heteroaryl($C_{1-6}$)alkyl, either of which groups may be optionally substituted.

Suitable values for the substituent $R^2$ in the compounds according to the invention include cyclohexylmethyl, benzyl, pyrazolylmethyl, isoxazolylmethyl, thiazolylmethyl, thiazolylethyl, imidazolylmethyl, benzimidazolylmethyl, oxadiazolylmethyl, triazolylmethyl, tetrazolylmethyl, pyridinylmethyl, pyridazinylmethyl, pyrimidinylmethyl, pyrazinylmethyl, quinolinylmethyl, isoquinolinylmethyl and quinoxalinylmethyl, any of which groups may be optionally substituted by one or more substituents.

Suitably, $R^2$ represents an optionally substituted triazolylmethyl group.

Examples of suitable optional substituents on the group $R^2$ include $C_{1-6}$ alkyl, aryl($C_{1-6}$)alkyl, pyridyl($C_{1-6}$)alkyl, halogen, halo($C_{1-6}$)alkyl, cyano, cyano($C_{1-6}$)alkyl, hydroxymethyl, $C_{1-6}$ alkoxy, $C_{3-7}$ cycloalkyl($C_{1-6}$)alkoxy, amino($C_{1-6}$)alkyl, di($C_{1-6}$)alkylamino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl ($C_{1-6}$)alkyl and di($C_{1-6}$)alkylmorpholinyl($C_{1-6}$)alkyl.

Specific illustrations of particular substituents on the group $R^2$ include methyl, ethyl, n-propyl, benzyl, pyridinylmethyl, chloro, chloromethyl, cyano, cyanomethyl, hydroxymethyl, ethoxy, cyclopropylmethoxy, dimethylaminomethyl, aminoethyl, dimethylaminoethyl, dimethylaminocarbonylmethyl, N-methylpiperidinyl, pyrrolidinylethyl, piperazinylethyl, morpholinylmethyl and dimethylmorpholinylmethyl, especially methyl or ethyl, and more specially methyl.

Representative values of $R^2$ include hydroxymethyl-cyclohexylmethyl, cyanobenzyl, hydroxymethyl-benzyl, pyrazolylmethyl, dimethyl-pyrazolylmethyl, methyl-isoxazolylmethyl, thiazolylmethyl, methyl-thiazolylmethyl, ethyl-thiazolylmethyl, methyl-thiazolylethyl, imidazolylmethyl, methyl-imidazolylmethyl, ethyl-imidazolylmethyl, benzyl-imidazolylmethyl, benzimidazolylmethyl, methyl-oxadiazolylmethyl, triazolylmethyl, methyl-triazolylmethyl, ethyl-triazolylmethyl, propyl-triazolylmethyl, benzyl-triazolylmethyl, pyridinylmethyl-triazolylmethyl, cyanomethyl-triazolylmethyl, dimethylaminomethyl-triazolylmethyl, aminoethyl-triazolylmethyl, dimethylaminoethyl-triazolylmethyl, dimethylaminocarbonylmethyl-triazolylmethyl, N-methylpiperdinyl-triazolylmethyl, pyrrolidinylethyl-triazolylmethyl, piperazinylethyl-triazolylmethyl, morpholinylethyl-triazolylmethyl, methyl-tetrazolylmethyl, pyridinylmethyl, methyl-pyriadinylmethyl, dimethyl-pyridiaylmethyl, ethoxy-pyridinylmethyl, cpyclopropylmethoxy-pyrldinylmethyl, pyridazi nylmethyl, chloro-pyridazinylmethyl, pyrimidinylmethyl, pyrazinylmethyl, quinolinylmethyl, isoquinolinylmethyl and quinoxalinylmethyl.

Particular values of $R^2$ include methyl-triazolylmethyl and ethyl-triazolylmethyl.

A favoured value of $R^2$ is methyl-triazolylmethyl.

A particular sub-class of compounds according to the invention is represented by the compounds of formula IIA, and salts and prodrugs thereof:

(IIA)

wherein $R^1$ is as defined above;
n is 1 or 2, typically 1; and
$R^{12}$ represents aryl or heteroaryl, either of which groups may be optionally substituted.

Suitably, $R^{12}$ represents phenyl, pyrazolyl, isoxazolyl, thiazolyl, imidazolyl, benzimidazolyl, oxadiazolyl, triazolyl, tetrazolyl, pyridinyl, pydazinyl, pyrimidinyl, pyrazinyl, quinolinyl, isoquinolinyl or quinoxalinyl, any of which groups may be optionally substituted.

A particular value of $R^{12}$ is optionally substituted triazolyl.

Examples of typical substituents on the group $R^{12}$ include $C_{1-6}$ alkyl, aryl($C_{1-6}$)alkyl, pyridyl($C_{1-6}$)alkyl, halogen, cyano, cyano($C_{1-6}$)alkyl, hydroxymethyl, $C_{1-6}$ alkoxy, $C_{3-7}$ cycloalkyl($C_{1-6}$)alkoxy, di($C_{1-6}$)alkylamino($C_{1-6}$)alkyl, amino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl and morpholinyl($C_{1-6}$)alkyl.

Illustrative values of specific substituents on the group $R^{12}$ include methyl, ethyl, n-propyl, benzyl, pyridinylmethyl, chloro, cyano, cyanomethyl, hydroxymethyl, ethoxy, cyclopropylmethoxy, dimethylaminomethyl, aminoethyl, dimethylaminoethyl, dimethylaminocarbonylmethyl, N-methylpiperidinyl, pyrrolidinylethyl, piperazinylethyl and morpholinylmethyl, especially methyl or ethyl, and more especially methyl.

Representative values of $R^{12}$ include cyanophenyl, hydroxymethyl-phenyl, pyrazolyl, dimethyl-pyrazolyl, methyl-isoxazolyl, thiazolyl, methyl-thiazolyl, ethyl-thiazolyl, imidazolyl, methyl-imidazolyl, ethyl-imidazolyl, benzyl-imidazolyl, benzimidazolyl, methyl-oxadiazolyl, triazolyl, methyl-triazolyl, ethyl-triazolyl, propyl-triazolyl, benzyl-triazolyl, pyridinylmethyl-triazolyl, cyanomethyl-triazolyl, dimethylaminomethyl-triazolyl, aminoethyl-triazolyl, dimethylaminoethyl-triazolyl, dimethylaminocarbonylmethyl-triazolyl, N-methylpiperidinyl-triazolyl, pyrrolidinylethyl-triazolyl, pip erazinylethyl-triazolyl, morpholinylethyl-triazolyl, methyl-tetrazolyl, pyridinyl, methyl-pyridinyl, dimethyl-pyridinyl, ethoxy-pyridinyl, cyclopropylmethoxy-pyridinyl, pyridazinyl, chloro-pyridazinyl, pyrimidinyl, pyrazinyl, quinolinyl, isoquinolinyl and quinoxalinyl.

Particular values of $R^{12}$ include methyl-triazolyl and ethyl-triazolyl.

A favoured value of $R^{12}$ is methyl-triazolyl.

A particular subset of the compounds of formula IIA above is represented by the compounds of formula IIB, and pharmaceutically acceptable salts thereof:

(IIB)

wherein
$R^1$ is as defined with reference to formula I above; and
$R^5$ represents hydrogen, methyl or ethyl.

In relation to formula IIB above, $R^1$ suitably represents phenyl or fluorophenyl.

In one embodiment of the compounds of formula IIB above, $R^5$ represents hydrogen or methyl.

Suitably, $R^5$ represents methyl or ethyl, especially methyl.

Another sub-class of compounds according to the invention is represented by the compounds of formula IIC, and salts and prodrugs thereof:

(IIC)

wherein
$R^1$ is as defined with reference to formula I above;
n and $R^{12}$ are as defined with reference to formula IIA above; and
$Z^1$ represents $C_{1-6}$ alkyl, $C_{3-7}$ cycloalkyl or aryl, any of which groups may be optionally substituted.

Examples of typical substituents on the group $Z_1$ include $C_{1-6}$ alkyl, especially methyl.

Illustrative values for the groups $Z_1$ include methyl, ethyl, isopropyl, tert-butyl, 1,1-dimethylpropyl, cyclopropyl, methyl-cyclopropyl, cyclobutyl, methyl-cyclobutyl, cyclopentyl, methyl-cyclopentyl, cyclohexyl and phenyl.

Particular values of $Z_1$ include tert-butyl, cyclobutyl and phenyl.

In a specific embodiment, $Z_1$ represents cyclobutyl. In another embodiment, $Z_1$ represents phenyl.

A particular subset of the compounds of formula IIC above is represented by the compounds of formula IID, and salts and prodrugs thereof:

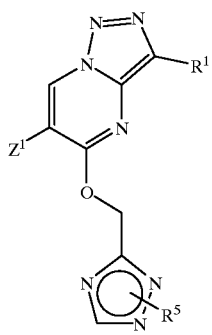

(IID)

wherein
  $R^1$ is as defined with reference to formula I above;
  $R^5$ is as defined with reference to formula IIB above; and
  $Z^5$ is as defined with reference to formula IIC above.

Specific compounds within the scope of the present invention include:
  3-(2-fluorophenyl)-5-(2-methyl-2H-1,2,4-triazol-3-ylmethoxy)-1,2,3-triazolo[1,5-α]quinazoline;
  3-(2-fluorophenyl)-5-(2-methyl-2H-1,2,4-triazol-3-ylmethoxy)-6-phenyl-1,2,3-triazolo[1,5-α]pyrimidine;
  6-cyclobutyl-3-(2-fluorophenyl)-5-(2-methyl-2H-1,2,4-triazol-3-ylmethoxy)-1,2,3-triazolo[1,5-α]pyrimidine;
  6-cyclobutyl-3-(2-fluorophenyl)-5-(1-methyl-1H-1,2,4-triazol-3-ylmethoxy)-1,2,3-triazolo[1,5-α]pyrimidine;
  6-cyclobutyl-5-(2-ethyl-2H-1,2,4-triazol-3-ylmethoxy)-3-(2-fluorophenyl)-1,2,3-triazolo[1,5-α]pyrimidine;
  3-(2-fluorophenyl)-5-(1-methyl-1H-1,2,4-triazol-3-ylmethoxy)-6-phenyl-1,2,3-triazolo[1,5-α]pyrimidine;
  5-(2-ethyl-2H-1,2,4-triazol-3-ylmethoxy)-3-(2-fluorophenyl)-6-phenyl-1,2,3-triazolo[1,5-α]pyrimidine;
  and salts and prodrugs thereof.

Also provided by the present invention is a method for the treatment and/or prevention of anxiety which comprises administering to a patient in need of such treatment an effective amount of a compound of formula I as defined above or a pharmaceutically acceptable salt thereof or a prodrug thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof or a prodrug thereof.

The binding affinity ($K^i$) of the compounds according to the present invention for the α3 subunit of the human $GABA_A$ receptor is conveniently as measured in the assay described hereinbelow. The α3 subunit binding affinity ($K_i$) of the compounds of the invention is ideally 10 nM or less, preferably 2 nM or less, and more preferably 1 nM or less.

The compounds according to the present invention will ideally elicit at least a 40%, preferably at least a 50%, and more preferably at least a 60%, potentiation of the GABA $EC_{20}$ response in stably transfected recombinant cell lines expressing the α3 subunit of the human $GABA_A$ receptor. Moreover, the compounds of the invention will ideally elicit at most a 30%, preferably at most a 20%, and more preferably at most a 10%, potentiation of the GABA $EC_{20}$ response in stably transfected recombinant cell lines expressing the α1 subunit of the human $GABA_A$ receptor.

The potentiation of the GABA EC20 response in stably transfected cell lines expressing the α3 and α1 subunits of the human $GABA_A$ receptor can conveniently be measured by procedures analogous to the protocol described in Wafford et al., *Mol. Pharinacol.*, 1996, 50, 670–678. The procedure will suitably be carried out utilising cultures of stably transfected eukaryotic cells, typically of stably transfected mouse Ltk fibroblast cells.

The compounds according to the present invention exhibit anxiolytic activity, as may be demonstrated by a positive response in the elevated plus maze and conditioned suppression of drinking tests (cf. Dawson et al., *Psychopharmacology*, 1995, 121, 109–117). Moreover, the compounds of the invention are substantially non-sedating, as may be confirmed by an appropriate result obtained from the response sensitivity (chain-pulling) test (cf. Bayley et al., *J. Psychopharinacol.*, 1996, 10, 206–213).

The compounds according to the present invention may also exhibit anticonvulsant activity. This can be demonstrated by the ability to block pentylenetetrazole-induced seizures in rats and mice, following a protocol analogous to that described by Bristow et al. in *J. Pharinacol. Exp. Ther.*, 1996, 279, 492–501.

In order to elicit their behavioural effects, the compounds of the invention will ideally be brain-penetrant; in other words, these compounds will be capable of crossing the so-called "blood-brain barrier". Preferably, the compounds of the invention will be capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions. and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of anxiety, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds of formula I as defined above may be prepared by a process which comprises reacting a compound of formula III with a compound of formula IV:

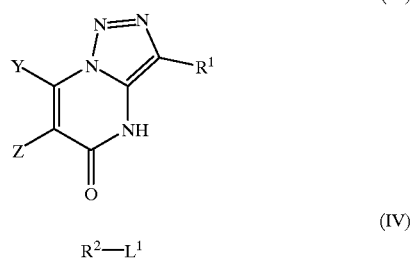

(III)

(IV)

wherein Y, Z, $R^1$ and $R^2$ are as defined above, and $L^1$ represents a suitable leaving group.

The leaving group $L^1$ is typically a halogen atom, especially chloro.

Alternatively, the leaving group $L^1$ may represent the moiety formed by reaction of a hydroxy group with triphenylphosphine in the presence of diethyl azodicarboxylate.

Where the leaving group $L^1$ represents a halogen atom, the reaction between compounds III and IV is conveniently effected by stirring the reactants in a suitable solvent, typically N,N-dimethylformamide, in the presence of a strong base such as sodium hydride or potassium bis(trimethylsilyl)amide.

Where the leaving group $L^1$ represents the moiety formed by reaction of a hydroxy group with triphenylphosphine in the presence of diethyl azodicarboxylate, the reaction between compounds III and IV is conveniently effected by stirring the reactants in a suitable solvent, e.g. tetrahydrofuran.

The intermediates of formula III above, in particular those wherein Y and Z are taken together with the two intervening carbon atoms to form a ring, may be prepared by reacting an azide derivative of formula V with an acetonitrile derivative of formula VI:

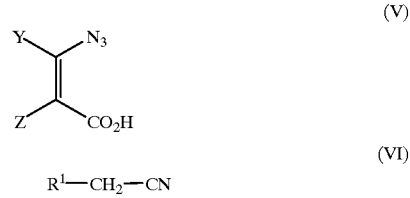

(V)

(VI)

wherein Y, Z and $R^1$ are as defined above.

The reaction between compounds V and VI is conveniently effected under basic conditions in a suitable solvent, for example sodium ethoxide in ethanol, typically at an elevated temperature.

The intermediates of formula V may be prepared by diazotisation of a compound of formula VII:

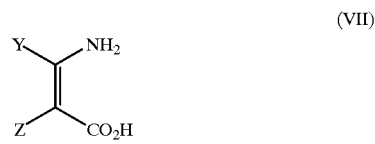

(VII)

wherein Y and Z are as defined above; followed by displacement with azide ion.

The diazotisation/displacement procedure is conveniently effected by treating compound VII with sodium nitrite at 0° C. in the presence of a mineral acid, e.g. hydrochloric acid, then with sodium azide, typically in the presence of sodium acetate.

In an alternative approach, the intermediates of formula III above, in particular those wherein Y and Z represent pendant groups (i.e. are not taken together with the intervening carbon atoms to form a ring), may be prepared by cyclising a compound of formula VIII:

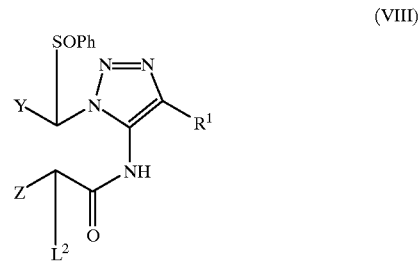

(VIII)

wherein Y, Z and $R^1$ are as defined above, $L^2$ represents a suitable leaving group, and Ph is an abbreviation for phenyl.

The leaving group $L^2$ is typically a halogen atom, especially chloro.

The cyclisation of compound VIII is conveniently effected by treatment with a strong base, e.g. potassium bis(trimethylsilyl)amide, in the presence of a suitable solvent, e.g. tetrahydrofuran, typically at a temperature in the region of −78° C.

The intermediates of formula VIII may be prepared by reacting a compound of formula IX with a compound of formula X:

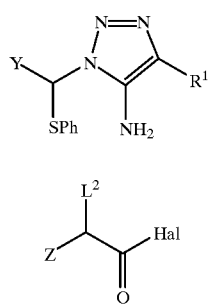

wherein Y, Z, $R^1$ and $L^2$ are as defined above, and Hal represents a halogen atom; followed by oxidation of the phenylthio group.

The halogen atom Hal in the compounds of formula X is typically chloro.

The reaction between compounds IX and X is conveniently carried out in a solvent such as N,N-dimethylformamide, typically in the presence of pyridine, and suitably at a temperature in the region of 0° C. Subsequent oxidation of the phenylthio group is conveniently accomplished by treatment with ozone, typically in dichloromethane at a temperature in the region of −78° C.

The intermediates of formula IX above may be prepared by reacting a compound of formula VI as defined above with a compound of formula XI:

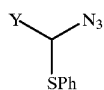

wherein Y is as defined above.

The reaction between compounds VI and XI is conveniently carried out by stirring the reactions in a suitable solvent, e.g. dimethylsulphoxide, typically in the presence of a base such as potassium carbonate.

Where they are not commercially available, the starting materials of formula IV, VI, VII, X and XI may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art. For example, a compound of formula I initially obtained wherein $R^2$ is unsubstituted may be converted into a corresponding compound wherein $R^2$ is substituted, typically by standard alkylation procedures, for example by treatment with a haloalkyl derivative in the presence of sodium hydride and N,N-dimethylformamide. or with a hydroxyalkyl derivative in the presence of triphenylphosphine and diethyl azodicarboxylate. Furthermore, a compound of formula I initially obtained wherein the $R^2$ substituent is substituted by a halogen atom, e.g. chloro, may be converted into the corresponding compound wherein the $R^2$ substituent is substituted by a di($C_{1-6}$)alkylamino moiety by treatment with the appropriate di($C_{1-6}$)alkylamine, typically with heating in a solvent such as 1,4-dioxane in a sealed tube.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups is Organic Synthesis*, John Wiley & Sons, 1991. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human $GABA_A$ receptors containing the β2 or α3 subunit stably expressed in Ltk cells.

Reagents

Phosphate buffered saline (PBS).

Assay buffer: 10 mM $KH_2PO_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells) in assay buffer.

Flunitrazepam 100 μM in assay buffer.

Cells resuspended in assay buffer (1 tray to 10 ml).

Harvestitg Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for of α1β3γ2: 1.8 nM; for α2β3γ2: 1.8 nM; for α3β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [$^3$H]-flumazenil from the α2 and/or α3 subunit of the human GABA$_A$ receptor of 100 nM or less.

EXAMPLE 1

3-(2-Fluorophenyl)-5-(2-methyl-2H-1,2,4-triazol-3-ylmethoxy)-1,2,3-triazolo[1,5-α]quinazoline (a) 3-(2-Fluorophenyl)-1,2,3-triazolo[1,5-α]quinazolin-5-one Sodium (0.55 g, 24 mmol) was dissolved in dry ethanol (25 ml) at room temperature under nitrogen. 2-Fluorophenylacetonitrile (1.9 ml, 15 mmol) was added and the orange solution was stirred for 15 min, followed by dropwise addition of a solution of 2-azidobenzoic acid (1.97 g, 12.1 mmol) in diy ethanol (20 ml). The thick, white gel was stirred at room temperature for 45 min then refluxed for 18 h. Solvent was removed by evaporation and water (40 ml) was added. The yellow suspension was acidified with aqueous citric acid (1 M). The precipitate was collected, washed with water and dried in vacuo at room temperature to give 3-(2-fluorophenyl)-1,2,3-triazolo[1,5-α]quinazolin-5-one (3.38 g, 100%) as an off-white powder, m.p. 238–241° C. (DMF). Found: C, 64.33; H, 3.06; N, 20.29. $C_{15}H_9FN_4O$ requires C, 64.28; H, 3.24; N, 19.99%. $\delta_H$ (360 MHz; DMSO) 7.33–7.38 (2H, m), 7.46–7.55 (1H, m), 7.69–7.73 (2H, m), 8.02 (1H, ddd, J=9, 9 and 1), 8.24 (1H, dd, J=8 and 1), 8.38 (1H, d, J=8) and 12.40 (1H, br s); m/z (ES$^+$) 821 (M+H$^+$).

(b) 3-(2-Fluorophenyl)-5-(2-methyl-2H-1, 2,4-triazol-3-ylmethoxy)-1,2,3-triazolo[1,5-α]quinazoline A solution of potassium hexamethyldisilazide in toluene (0.5 M, 4 ml, 2.0 mmol) was added at room temperature under nitrogen to a stirred solution of 3-(2-fluorophenyl)-1, 2,3-triazolo[1,5-α]quinazolin-5-one (0.56 g, 2.0 mmol) in dry DMF (10 ml). The dark brown solution was stirred for 10 min followed by addition of a solution of 2-methyl-3-chloromethyl-1,2,4-triazole (0.35 g, 2.65 mmol) in dry DMF (3 ml). The red solution was stirred at room temperature for 3 days, then poured into water (120 ml) and the yellow precipitate collected. The material was dissolved in dichloromethane (50 ml), dried (Na$_2$SO$_4$), filtered and concentrated. Flash column chromatography on silica gel, eluting with 5% methanol-dichloromethane, partly removed unreacted starting material. The crude product was hot-filtered and recrystallised from ethyl acetate to give 3-(2-fluorophenyl)-5-(2-methyl-2H-1,2,4-triazol-3-ylmethoxy)-1,2,3-triazolo[1,5-α]quinazoline (0.354 g, 47%) as a very pale yellow solid, m.p. 195–197° C. Found: C, 60.14; H, 3.61; N, 25.86. $C_{19}H_{14}FN_7O \cdot 0.25(H_2O)$ requires C, 60.08; H, 3.85; N, 25.81%. $\delta_H$ (360 MHz; DMSO) 3.94 (3H, s), 5.82 (2H, s), 7.37–7.43 (2H, m), 7.46–7.58 (1H, m), 7.82 (1H, dd, J=7 and 7), 7.97 (1H, s), 8.01 (1H, ddd, J=7, 7 and 1), 8.16 (1H, ddd, J=8, 8 and 1), 8.29 (1H, d, J=8) and 8.61 (1H, d, J=8); m/z (ES+) 376 (M+H+).

EXAMPLE 2

3-(2-Fluoroihenyl)-5-(2-methyl-2H-1,2,4-triazol-3-ylmethoxy)-6-phenyl1,2,3-triazolo[1,5-α]pyrimidine (a) 5-(2-FluoroDhenyl)-3-phenylsulfenylmethyl-3H-1,2,3-triazol-4-ylamine To a stirred suspension of potassium carbonate (19.5 g, 141 mmol) in dry dimethylsulfoxide (100 ml) under nitrogen was added 2-fluorophenylacetonitrile (5.9 ml, 46 mmol). The reaction was stirred for 5 minutes at which time azidomethyl phenyl sulfide (5 ml, 35.3 mmol) was added dropwise. The resulting yellow reaction mixture was stirred at room temperature for 16 hours before slow addition to distilled water (2000 ml) with vigorous stirring. The aqueous mixture was extracted with ethyl acetate (4×500 ml) and the combined organic extracts were washed with brine (500 ml), dried (Na$_2$SO$_4$) and the solvent removed in vacuo. The resultant brown oil was purified by flash chromatography (25% EtOAc/isohexane) and the product crystallised from diethyl ether to furnish 5-(2-fluorophenyl)-3-phenylsulfenylmethyl-3H-1,2,3-triazol-4-ylamine (3.04 g, 29%) as a pale yellow solid. $\delta_H$ (400 MHz, CDCl$_3$) 4.10 (2H, br s, NH$_2$), 5.55 (2H, s, PhSCH$_2$), 7.11 (1H, ddd, J=11.5, 8.2 and 1, ArH), 7.22–7.32 (5H, m, ArH), 7.39–7.41 (2 H, m, ArH), 7.89 (1H, td, J=7.5 and 2.0, ArH); m/z (ES$^+$) 301 (M+H$^+$).

(b) 2-Chloro-N-[5-(2-fluorophenyl)-3-phenyisulfenylmethyl-3H-1,2,3-triazol-4-yl]-2-phenylacetamide To a cold (0° C.), stirred solution of 5-(2-fluorophenyl)-3-phenylsulfenylmethyl-3H-1,2,3-triazol-4-ylamine (1.30 g, 4.32 mmol) in dimethylformamide (30 ml) under nitrogen was added pyridine (0.46 ml, 5.62 mmol) followed by rac-α-chlorophenylacetyl chloride (0.79 ml, 4.97 mmol). The reaction mixture was stirred at 0° C. for 1 hour and subsequently poured into distilled water (200 ml). The aqueous solution was extracted with ethyl acetate (2×100 ml) and the combined organic extracts were washed with citric acid (100 ml, 10% aqueous), sodium hydrogencarbonate (100 ml, sat. aqueous), water (100 ml), brine (100 ml) and dried (Na$_2$SO$_4$). The solvent was removed in vacuo and the resulting oil was crystallised from hot diethyl ether to afford 2-chloro-N-[5-(2-fluoro-phenyl)-3-phenylsulfenylmethyl-3H-1,2,3-triazol-4-yl]-2-phenylacetamide (1.514 g, 78%) as a pale solid. $\delta_H$ (400 MHz, CDCl$_3$) 5.37 (1H, s, CHCl), 5.49 (1 H, d, J=14.4, PhSCH$_{2A}$), 5.61 (1H, d, J=14.4, PhSCH$_{2B}$), 7.11 (1H, dd, J=11 and 8.6, ArH), 7.24–7.44 (12H, m, ArH), 7.82 (1H, td, J=7.6 and 1.4, ArH), 8.21–8.19 (1H, m, NH); m/z (ES$^+$) 453 ($^{35}$ClM+H$^+$) and 455 ($^{37}$ClM+H+).

(c) N-[3-Benzenesulfinylmethyl-5-(2-fluorophenyl)-3H-1,2,3-triazol-4-yl]-2-chloro-2-phenylacetamide A solution of 2-chloro-N-[5-(2-fluorophenyl)-3-phenylsulfenyl-methyl-3H-1,2,3-triazol-4-yl]-2-phenylacetamide (1.48 g, 3.27 mmol) in dichloromethane (100 ml) was cooled to −78° C. and a stream of ozone gas in oxygen bubbled through the solution. After 4 hours tlc analysis indicated complete consumption of starting materials and the stream of ozone was ceased. The reaction mixture was allowed to warm to room temperature and the solvent removed in vacuo to afford N-[3-benzenesulfinylmethyl-5-(2-fluorophenyl)-3H-1,2,3-triazol-4-yl]-2-chloro-2-phenylacetamide as a pale yellow foam and as a 1:1 mixture of diastereomers. The compound was used in subsequent reactions without further purification. $\delta_H$ (400 MHz, CDCl$_3$) 5.21–5.51 (3H, m, CH$_2$S(=O)Ph+CHCl), 6.98–7.04 (1H, m, ArH), 7.19 (1H, t, J=7.5, ArH), 7.29–7.60 (11H, m, ArH), 7.74 (1H, t, J=7.5, Ar H), 9.80 and 9.84 (1H, s, NH); m/z (ES$^+$) 469 ($^{35}$ClM+H$^+$) and 471 ($^{37}$ClM+H$^+$).

(d) 3-(2-Fluorophenyl)-6-phenyl-4H-1,2,3-triazolo[1,5-α]pyrimidin-5-one

To a cold (−78° C.), stirred solution of N-[3-benzenesulfinylmethyl-5-(2-fluorophenyl)-3H-1,2,3-triazol-4-yl]-2-chloro-2-phenylacetamide (850 mg, 1.81 mmol) in dry tetrahydrofuran (50 ml) was added a solution of potassium bis(trimethylsilyl)amide (8.44 ml, 0.752 M in toluene, 6.34 mmol) and the reaction stirred for 90 minutes. The reaction was then transferred to a −20° C. bath and stirred for 15 minutes. The reaction was quenched by pouring into water (200 ml) and stirring for 10 minutes. The aqueous mixture was acidified with citric acid (10% aqueous) and extracted with ethyl acetate (2×200 ml). The combined organic extracts were washed with water (100 ml), brine (100 ml), dried ($Na_2SO_4$) and concentrated iin vacuo to about 10 ml total volume. 3-(2-Fluorophenyl)-6-phenyl-4H-1,2,3-triazolo[1,5-α]pyrimidin-5-one (355 mg, 64%) thus obtained was collected by filtration and washed with diethyl ether. The title product was used in subsequent reactions without further purification. $δ_H$ (400 MHz, DMSO) 7.32–7.39 (6H, m, ArH, 7.70–7.74 (3H, m, ArH), 9.17 (1H, s, PhC=CH), 12.70 (1H, br s, NH); m/z (ES$^+$) 307 (M+H$^+$).

(e) 3-(2-Fluorophenyl)-5-(2-methyl-2H-1,2,4-triazol-3-ylmethoxy)-6-Phenyl-1,2,3-triazolo[1,5-α]pyrimidine 3-(2-Fluorophenyl)-6-phenyl-4H-1,2,3-triazolo[1,5-α] pyrimidin-5-one (10 mg, 0.033 mmol), triphenylphosphine (21 mg, 0.08 mmol) and (2-methyl-2H-1,2,4-triazol-3-yl) methanol (11 mg, 0.087 mmol) were suspended at room temperature in dry tetrahydrofuran (0.5 ml). Diethyl azodicarboxylate (15 μl, 0.095 mmol) was added at which point a clear yellow solution resulted. The reaction was stirred at room temperature for 64 hours before purification by preparative thin layer chromatography to afford 3-(2-fluorophenyl)-5-(2-methyl-2H-1,2,4-triazol-3-ylmethoxy)-6-phenyl-1,2,3-triazolo[1,5-α]pyrimidine (5 mg, 39%) as a white solid. $δ_H$ (400 MHz, $CDCl_3$) 3.79 (3H, s, NMe, 5.69 (2H, s, OCH$_2$), 7.24 (1H, td, J=9.2 and 1.2 Hz, ArH), 7.31 (1H, td, J=8.4 and 1.3 Hz, ArH), 7.39–7.43 (1H, m, ArH), 7.48–7.51 (3H, m, ArH), 7.54–7.58 (2H, m, ArH), 7.86 (1H, s, CH-triazole), 8.00 (1H, td, J=8.3 and 2.0 Hz, ArH), 8.80 (1H, s, PhC=CH);m/z (ES$^+$) 402 (M+H$^+$).

EXAMPLE 3

6-Cyclobutyl-3-(2-fluorophenyl)-5-(2-methyl-2H-1,2,4-triazol-3-ylmethoxy)-1,2,3-triazolo[1,5-α]pyrimidine (a) 2-Chloro-2-cyclobutyl-N-[5-(2-fluorophenyl)-3-phenylsulfenylmethyl-3H-1,2,3-triazol-4-yl]acetamide To a cooled (0° C.), stirred solution of 5-(2-fluorophenyl)-3-phenylsulfenylmethyl-3H-1,2,3-triazol-4-ylamine (1 g, 3.33 mmol) in dimethylformamide (15 ml) was added pyridine (460μl, 4.33 mmol) followed by 2-chloro-2-cyclobutylacetyl chloride (810 mg, 3.83 mmol) and the reaction stirred at 0° C. for 1 hour. The reaction was quenched by partitioning between ethyl acetate (100 ml) and water (100 ml). The layers were separated and the aqueous layer extracted with ethyl acetate (100 ml). The combined organic extracts were washed with citric acid (50 ml, 10% aqueous), sodium bicarbonate (50 ml, sat. aqueous), brine (50 ml). dried ($Na_2SO_4$) and the solvent removed in vacuo. The crude product was purified by flash chromatography (40% EtOAc/hexanes) to afford 2-chloro-2-cyclobutyl-N-[5-(2-fluorophenyl)-3-phenylsulfenylmethyl-3H-1,2,3-triazol-4-yl]acetamide (450 g, 31%; 52% based on recovered starting material) as a crystalline solid, m.p. 103–104° C.; δH (400 MHz, $CDCl_3$) 1.79–2.18 (6H, m, CH(CH$_2$)$_3$), 2.83–2.93 (1H, m, CH(CH$_2$)$_3$), 4.28 (1H, d, J=8 Hz, CHCl), 5.58 (1H, d, J=14.3 Hz, PhSCH$_{2A}$), 5.64 (1H, d, J=14.3 Hz, PhSCH$_{2B}$), 7.10–7.16 (1H, m, ArH), 7.23–7.41 (7H, m, Ar H), 7.79–7.85 (1H, m, ArH), 8.00–8.10 (1H, br m, NH); m/z (ES$^+$) 431 (100%) ($^{35}$ClM+H$^+$), 433 (40%) ($^{37}$ ClM+H+).

(b) N-[3-Benzenesulfinylmethyl-5-(2-fluorophenyl)-3H-1,2,3-triazol-4-yl]-2-chloro-2-cyclobutylacetamide A solution of 2-chloro-2-cyclobutyl-N-[5-(2-fluorophenyl)-3-phenylsulfenylmethyl-3H-1,2,3-trlazol-4-yl]acetamide (300 mg, 0.7 mmol) in dichloromethane (100 ml) was cooled to −78° C. and a stream of ozone gas in oxygen bubbled through the solution. After 90 minutes tlc analysis indicated complete consumption of starting materials and the stream of ozone was ceased. The reaction mixture was allowed to warm to room temperature and the solvent removed iit vacuo to afford N-[3-benzenesulfinylmethyl-5-(2-fluorophenyl)-3H-1,2,3-triazol-4-yl]-2-chloro-2-cyclobutylacetamide as a white foam and as a mixture of diastereomers. The compound was used in subsequent reactions without further purification. $δ_H$ (400 MHz, $CDCl_3$) 1.80–2.25 (6H, m, CH(CH$_2$)$_3$), 2.90–3.05 (1H, m, CH(CH$_2$)$_3$), 4.34 (1Ha, d, J=8.2 Hz, aC HCl), 4.35 (1HA, d, J=8.2 Hz, ACHCl), 5.25–5.35 (1H, m, PhS=OCH$_{2A}$), 5.49–5.59 (1H, m, PhS=OCH$_{2B}$), 7.07–7.12 (1H, m, ArH), 7.24 (1H, t, J=7.4 Hz, ArH), 7.34–7.39 (1H, m, ArH), 7.49–7.57 (5H, m, ArH), 7.78–7.84 (1H, m, ArH), 9.70 (1H, s, NH; m/z (ES$^+$) 447 (100%) ($^{35}$ClM+H$^+$), 449 (40%) ($^{37}$ClM+H$^+$).

(c) 6-Cyclobutyl-3-(2-fluorophenyl)-4H-1,2,3-triazolo[1,5-α]pyrimidin-5-one

To a cold (−78° C.), stirred solution of N-[3-benzenesulfinylmethyl-5-(2-fluorophenyl)-3H-1,2,3-triazol-4-yl]-2-chloro-2-cyclobutylacetamide (166 mg. 0.37 mmol) in dry tetrahydrofuran (20 ml) under nitrogen was added a solution of potassium bis(trimethylsilyl)amide (1.8 ml, 0.752 M in toluene, 1.3 mmol) and the reaction stirred for 2 hours. The reaction was allowed to warm to −20° C. and maintained at this temperature for 45 minutes before quenching by careful addition to water (100 ml). The aqueous mixture was stirred for 5 minutes and then acidified with citric acid solution (25 ml, 10% aqueous). The aqueous was extracted with ethyl acetate (2×70 ml) and the combined organic extracts were washed with water (50 l), brine (50 l), dried ($Na_2SO_4$) and evaporated in vacuo to approximately 2 ml total volume. The concentrated solution was allowed to stand at room temperature for 16 hours. The solid precipitate thus formed was collected by filtration and washed with diethyl ether to afford 6-cyclobutyl-3-(2-fluorophenyl)-4H-1,2,3-triazolo[1,5-α]pyrimidin-5-one (45 mg, 43%) as a pale solid which was used in subsequent reactions without further purification. $δ_H$ (400 MHz, d$_6$-DMSO) 1.78–1.89 (1H, m, CH(CH$_2$)$_3$), 1.93–2.0 4(1H, m, CH(CH$_2$)$_3$), 2.11–2.31 (4H, m, CH(CH$_2$)$_3$), 3.47 (1H, quintet, J=8.6 Hz, CH(CH$_2$)$_3$), 7.30–7.35 (2H, m, ArH, 7.44–7.50 (1H, m, ArH), 7.69 (1H, t, J=7.2 Hz, ArH), 8.82 (1H, s, CH=C.), 12.33 (1H, br s, N H); m/z (ES$^+$) 285 (M+H$^+$).

(d) 6-Cyclobutyl-3-(2-fluoroohenyl)-5-(2-methyl-2H-1,2,4-triazol-3-ylmethoxy)-1,2,3-triazolo[1,5-α]pyrimidine 6-Cyclobutyl-3-(2-fluorophenyl)-4H-1,2,3-triazolo[1,5-α]pyrimidin-5-one (33 mg, 0.12 mmol), triphenylphosphine (76 mg, 0.29 mmol) and (2-methyl-2H-1,2,4-triazol-3-yl) methanol (37 mg, 0.29 mmol) were dissolved in dry tetrahydrofuran (1.5 ml) with stirring. Diethyl azodicarboxylate (46μl, 0.29 mmol) was added and the reaction stirred at room temperature for 16 hours before purification by preparative thin layer chromatography to afford 6-cyclobutyl-3-(2-fluorophenyl)-5-(2-methyl-2H-1,2,4-triazol-3-ylmethoxy)-1,2,3-triazolo[1,5-α]pyrimidine (31 mg, 70%) as a white crystalline solid, m.p. 181–184° C.; $δ_H$ (400 MHz, d$_6$-DMSO) 1.77–1.85 (1H, m, CH(CH$_2$)$_3$), 1.96–2.06 (1H, m, CH(CH$_2$)$_3$), 2.19–2.30 (4H, m, CH(CH$_2$)$_3$), 308 (1H, quintet, J=8.6 Hz, CH(CH$_2$)$_3$), 3.88 (3H, s, NMe, 5.65 (2H, s, OC$\underline{H}_2$), 7.34–7.38 (2H, m, Ar$\underline{H}$), 7.41–7.48 (1H, m, Ar$\underline{H}$), 7.94 (1H, s, triazole C$\underline{H}$), 7.97 (1H, t, J=7.2 Hz, Ar$\underline{H}$), 9.25 (1H, s, pyrimidine C$\underline{H}$); m/z (ES$^+$) 380 (M+H$^+$).

EXAMPLE 4

6-Cyclobutyl-3-(2-fluorophenyl)-5-(1-methyl-1H-1,2,4-triazol-3-ylmethoxy)-1,2,3-triazolo[1,5-α]pyrimidine 6-Cyclobutyl-3-(2-fluorophenyl)-4H-1,2,3-triazolo[1,5-α]pyrimidin-5-one (50 g, 0.18 mmol), triphenylphosphine (120 mg, 0.44 mmol) and (1-methyl-1H-1,2,4-triazol-3-yl)methanol (50 g, 0.44 mmol) were suspended in dry tetrahydrofuran (1.5 ml). Diethyl azodicarboxylate (70 μl, 0.44 mmol) was added and a solution resulted immediately. The reaction was stirred at room temperature for 48 hours during which time a precipitate formed in the reaction mixture. The crude reaction mixture was evaporated and recrystallised from EtOAc. The pale pink crystalline solid thus produced was collected by filtration and washed with diethyl ether to afford 6-cyclobutyl-3-(2-fluorophenyl)-5-(1-methyl-1H-1,2,4-triazol-3-ylmethoxy)-1,2,3-triazolo[1,5-α]pyrimidine (40 mg, 60%) as pale needles, m.p. 202–205° C.; δ$_H$ (400 MHz, CDCl$_3$) 1.84–1.92 (1H, m, CH(C$\underline{H}_2$)$_3$), 2.06–2.16 (3H, m, CH(C$\underline{H}_2$)$_3$), 3.67 (1H, quintet, J=9 Hz, C$\underline{H}$(CH$_2$)$_3$), 3.94 (3H, s, NC$\underline{H}_3$), 7.19–7.29 (2H, m, Ar$\underline{H}$), 7.32–7.36 (1H, m, Ar$\underline{H}$), 8.04 (1H, s, triazole C$\underline{H}$), 8.12 (1H, td, J=7.5 and 1.8 Hz, Ar$\underline{H}$), 8.55 (1H, d, J=1.5 Hz, pyrimidine C$\underline{H}$); m/z (ES$^+$) 380 (M+H$^+$).

EXAMPLE 5

6-Cyclobutyl-5-(2-ethyl-2H-1,2,4-triazol-3-ylmethoxy)-3-(2-fluorophenyl)-1,2,3-triazolo[1,5-α]pyrimidine 6-Cyclobutyl-3-(2-fluorophenyl)-4H-1,2,3-triazolo[1,5-α]pyrimidin-5-one (50 g, 0.18 mmol), triphenylphosphine (120 mg, 0.44 mmol) and (2-ethyl-2H-1,2,4-triazol-3-yl)methanol (60 mg, 0.44 mmol) were suspended in dry tetrahydrofuran (1.5 ml). Diethyl azodicarboxylate (70 μl, 0.44 mmol) was added and a solution resulted immediately. The reaction was stirred at room temperature for 48 hours before purification by preparative tlc (60% EtOAc/hexanes) to afford a colourless oil which crystallised upon the addition of diethyl ether. The white solid was collected by filtration and stirred in diethyl ether for 6 hours and collected by filtration to afford 6-cyclobutyl-5-(2-ethyl-2H-1,2,4-triazol-3-ylmethoxy)-3-(2-fluorophenyl)-1,2,3-triazolo[1,5-α]pyrimidine (41 mg; 59%) as white needles, m.p. 188–191° C.; δ$_H$ (360 MHz, CDCl$_3$) 1.42 (3H, t, J=7.3 Hz, NCH$_2$C$\underline{H}_3$), 1.89–1.94 (1H, m, CH(C$\underline{H}_2$)$_3$), 2.04–2.15 (3H, m, CH(C$\underline{H}_2$)$_3$), 2.36–2.43 (2H, m, CH(C$\underline{H}_2$)$_3$), 4.25 (2H, q, J=7.3 Hz, NC$\underline{H}_2$CH$_3$), 5.65 (2H, s, OC$\underline{H}_2$), 7.19–7.31 (2H, m, Ar$\underline{H}$), 7.36–7.42 (1H, m, Ar$\underline{H}$), 7.92 (1H, s, triazole C$\underline{H}$), 7.99 (1H, td, J=7.5 and 1.7 Hz, Ar$\underline{H}$), 8.59 (1H, d, J=1 Hz, pyrimidine C$\underline{H}$); m/z (ES$^+$) 394 (M+H$^+$).

EXAMPLE 6

3-(2-Fluorophenyl)-5-(1-methyl-1H-1,2,4-triazol-3-ylmethoxy)-6-phenyl-1,2,3-triazolo[1,5-α]pynrimidine 3-(2-Fluorophenyl)-6-phenyl-4H-1,2,3-triazolo[1,5-α]pyrimidin-5-one (77 mg, 0.25 mmol), triphenylphosphine (165 mg, 0.63 mmol) and (1-methyl-1H-1,2,4-triazol-3-yl)methanol (80 mg, 0.63 mmol) were suspended in dry tetrahydrofuran (1.5 ml). Diethyl azodicarboxylate (100 μl, 0.63 mmol) was added and a solution resulted immediately. The reaction was stirred at room temperature for 48 hours before purification by preparative tlc (40% EtOAc/hexanes) to give a white solid which was recrystallised from ethyl acetate/hexanes to afford 3-(2-fluorophenyl)-5-(1-methyl-1H-1,2,4-triazol-3-ylmethoxy)-6-phenyl-1,2,3-triazolo[1,5-α]pyrimidine (49 mg, 49%) as white needles, m.p. 170–171° C.; δ$_H$ (400 MHz, d$_6$-DMSO) 3.84 (3H, s, NC$\underline{H}_3$), 5.57 (2H, s, OC$\underline{H}_2$), 7.35–7.41 (2H, m, Ar$\underline{H}$), 7.43–7.51 (4H, m, Ar$\underline{H}$), 7.73 (2H, dd, J=8.1 and 1.8 Hz, Ar$\underline{H}$), 8.14 (1H, td, J=7.5 and 1.8 Hz, Ar$\underline{H}$), 8.45 (1H, s, triazole C$\underline{H}$), 9.51 (1H, s, pyrimidine C$\underline{H}$); m/z (ES$^+$) 402 (M+H$^+$).

EXAMPLE 7

5-(2-Ethyl-2H-1,2,4-triazol-3-ylmethoxy)-3-(2-fluorophenyl)-6-Dhenyl-1,2,3-triazolo[1,5-α]pyrimidine 3-(2-Fluorophenyl)-6-phenyl-4H-1,2,3-triazolo[1,5-α]pyrimidin-5-one (95 mg, 0.31 mmol), triphenylphosphine (203 mg, 0.78 mmol) and (2-ethyl-2H-1,2,4-triazol-3-yl)methanol (110 mg, 0.78 mmol) were suspended in dry tetrahydrofuran (1,5 ml). Diethyl azodicarboxylate (123 μl, 0.78 mmol) was added and a solution resulted immediately. The reaction was stirred at room temperature for 16 hours before purification by preparative tlc (40% EtOAc/hexanes) to give a white solid which was recrystallised from ethyl acetate/hexanes and triturated with diethyl ether to afford 5-(2-ethyl-2H-1,2,4-triazol-3-ylmethoxy)-3-(2-fluorophenyl)-6-phenyl-1,2,3-triazolo[1,5-α]pyrimidine (67 mg, 52%) as white plates, m.p. 147–148° C.; δ$_H$ (400 MHz, CDCl$_3$) 1.22 (3H, t, J=7.3 Hz, NCH$_2$CH$\underline{H}_3$), 4.13 (2H, q, J=7.3 Hz, NC$\underline{H}$2CH$_3$), 5.70 (2H, s, OCH$_2$), 7.24 (1H, t, J=29.3 Hz, Ar$\underline{H}$), 7.31 (1H, t, J=7.5 Hz. Ar$\underline{H}$), 7.41–7.48 (4H, m, Ar$\underline{H}$, 7.54–7.56 (2H, m, Ar$\underline{H}$), 7.89 (1H, s, triazole C$\underline{H}$), 8.02 (1H, td, J=7.5 and 1.7 Hz, Ar$\underline{H}$), 8.79 (1H, s, pyrimidine C$\underline{H}$); m/z (ES$^+$) 416 (M+H$^+$).

What is claimed is:

1. A compound of formula I, or a salt:

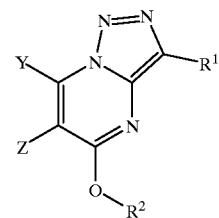

(I)

wherein

Y represents hydrogen or C$_{1-6}$alkyl optionally substituted with substituents independently selected from C$_{1-6}$alkyl, aryl(C$_{1-6}$)alkyl, pyridyl(C$_{1-6}$)alkyl, halogen, halo(C$_{1-6}$)alkyl, cyano, cyano(C$_{1-6}$)alkyl, hydroxy, hydroxymethyl, C$_{1-6}$alkoxy, C$_{3-7}$cycloalkyl(C$_{1-6}$) alkoxy, C$_{3-7}$cycloalkoxy, amino(C$_{1-6}$)alkyl, di(C$_{1-6}$) alkylamino(C$_{1-6}$)alkyl, di(C$_{1-6}$)alkylaminocarbonyl (C$_{1-6}$)alkyl, N-(C$_{1-6}$)alkylpiperidinyl, pyrrolidinyl(C$_{1-6}$)alkyl, piperazinyl(C$_{1-6}$)alkyl, morpholinyl(C$_{1-6}$) alkyl, di(C$_{1-6}$)alkylmorpholinyl(C$_{1-6}$)alkyl and imidazolyl(C$_{1-6}$)alkyl; and Z represents C$_{1-6}$alkyl, C$_{3-7}$cycloalkyl, C$_{4-7}$cycloalkenyl, C$_{6-8}$bicycloalkyl, aryl, C$_{3-7}$heterocyloalkyl, heteroaryl, C$_{2-7}$alkoxycarbonyl or di(C$_{1-6}$)alkylamino, any of which groups may be optionally substituted with substituents independently selected from C$_{1-6}$alkyl, aryl (C$_{1-6}$)alkyl, pyridyl(C$_{1-6}$)alkyl, halogen, halo(C$_{1-6}$) alkyl, cyano, cyano(C$_{1-6}$)alkyl, hydroxy, hydroxymethyl, C$_{1-6}$alkoxy, C$_{3-7}$cycloalkyl(C$_{1-6}$) alkoxy, C$_{3-7}$cycloalkoxy, amino(C$_{1-6}$)alkyl, di(C$_{1-6}$)

alkylamino($C_{1-6}$)alkyl, di($C_{1-6}$)alkylaminocarbonyl ($C_{1-6}$)alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl, di($C_{1-6}$)alkylmorpholinyl($C_{1-6}$)alkyl and imidazolyl($C_{1-6}$)alkyl; or Y and Z are taken together with the two intervening carbon atoms to form a ring selected from $C_5$cycloalkenyl, $C_{6-10}$bicycloalkenyl, tetrahydropyridinyl, pyridinyl and phenyl, any of which rings may be optionally benzo-fused and/or substituted with substituents independently selected from $C_{1-6}$alkyl, aryl($C_{1-6}$)alkyl, pyridyl($C_{1-6}$)alkyl, halogen, halo($C_{1-6}$)alkyl, cyano, cyano($C_{1-6}$)alkyl, hydroxy, hydroxymethyl, $C_{1-6}$alkoxy, $C_{3-7}$cycloalkyl($C_{1-6}$)alkoxy, $C_{3-7}$cycloalkoxy, amino($C_{1-6}$)alkyl, di($C_{1-6}$)alkylamino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl, di($C_{1-6}$)alkylmorpholinyl($C_{1-6}$)alkyl and imidazolyl($C_{1-6}$)alkyl;

$R^1$ represents $C_{3-7}$cycloalkyl, phenyl, furyl, thienyl or pyridinyl, any of which groups may be optionally substituted with substituents independently selected from $C_{1-6}$alkyl, aryl($C_{1-6}$)alkyl, pyridyl($C_{1-6}$)alkyl, halogen, halo($C_{1-6}$)alkyl, cyano, cyano($C_{1-6}$)alkyl, hydroxy, hydroxymethyl, $C_{1-6}$alkoxy, $C_{3-7}$cycloalkyl($C_{1-6}$)alkoxy, $C_{3-7}$cycloalkoxy, amino($C_{1-6}$)alkyl, di($C_{1-6}$)alkylamino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl, di($C_{1-6}$)alkylmorpholinyl($C_{1-6}$)alkyl and imidazolyl($C_{1-6}$)alkyl; and $R^2$ represents $C_{3-7}$cycloalkyl($C_{1-6}$)alkyl, aryl($C_{1-6}$)alkyl or heteroaryl($C_{1-6}$)alkyl, any of which groups may be optionally substituted with substituents independently selected from $C_{1-6}$alkyl, aryl($C_{1-6}$)alkyl, pyridyl($C_{1-6}$)alkyl, halogen, halo($C_{1-6}$)alkyl, cyano, cyano($C_{1-6}$)alkyl, hydroxy, hydroxymethyl, $C_{1-6}$alkoxy, $C_{3-7}$cycloalkyl($C_{1-6}$)alkoxy, $C_{3-7}$cycloalkoxy, amino($C_{1-6}$)alkyl, di($C_{1-6}$)alkylamino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl, di($C_{1-6}$)alkylmorpholinyl($C_{1-6}$)alkyl and imidazolyl($C_{1-6}$)alkyl.

2. A compound as claimed in claim 1 represented by formula IIA, and salts:

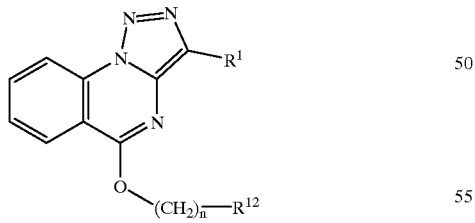

(IIA)

wherein $R^1$ is as defined in claim 1;
n is 1 or 2; and
$R_{12}$ represents aryl or heteroaryl, either of which groups may be optionally substituted with substituents independently selected from $C_{1-6}$alkyl, aryl($C_{1-6}$)alkyl, pyridyl($C_{1-6}$)alkyl, halogen, cyano, cyano($C_{1-6}$)alkyl, hydroxymethyl, $C_{1-6}$alkoxy, $C_{3-7}$cycloalkyl($C_{1-6}$)alkoxy, di($C_{1-6}$)alkylamino($C_{1-6}$)alkyl, amino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, and morpholinyl($C_{1-6}$)alkyl.

3. A compound as claimed in claim 2 represented by formula IIB, or a pharmaceutically acceptable salt thereof:

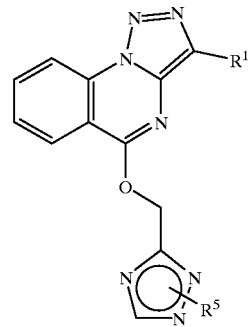

(IIB)

wherein
$R^5$ represents hydrogen, methyl or ethyl.

4. A compound as claimed in claim 1 represented by formula IIC, or a salt:

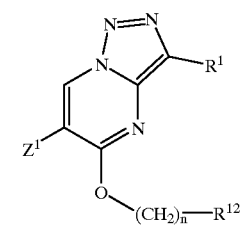

(IIC)

wherein
n is 1 or 2;
$R^{12}$ represents aryl or heteroaryl, either of which groups may be optionally substituted with substituents independently selected from $C_{1-6}$alkyl, aryl($C_{1-6}$)alkyl, pyridyl($C_{1-6}$)alkyl, halogen, cyano, cyano($C_{1-6}$)alkyl, hydroxymethyl, $C_{1-6}$alkoxy, $C_{1-6}$cycloalkyl($C_{1-6}$)alkoxy, di($C_{1-6}$)alkylamino($C_{1-6}$)alkyl, amino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, and morpholinyl($C_{1-6}$)alkyl; and
$Z^1$ represents $C_{1-6}$alkyl, $C_{3-7}$cycloalkyl or aryl, any of which groups may be optionally substituted with substituents independently selected from $C_{1-6}$alkyl.

5. A compound as claimed in claim 4 represented by formula IID, thereof:

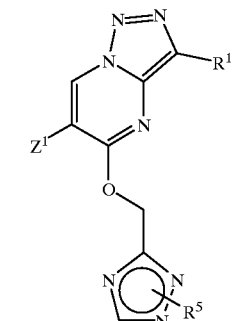

(IID)

wherein
$R^5$ represents hydrogen, methyl or ethyl.

6. A compound selected from:

3-(2-fluorophenyl)-5-(2-methyl-2H-1,2,4-triazol-3-ylmethoxy)-1,2,3-triazolo[1,5-α]quinazoline; and salts thereof.

7. A compound selected from:

3-(2-fluorophenyl)-5-(2-methyl-2H-1,2,4-triazol-3-ylmethoxy)-6-phenyl-1,2,3-triazolo[1,5-α]pyrimidine;

6-cyclobutyl-3-(2-fluorophenyl)-5-(2-methyl-2H-1,2,4-triazol-3-ylmethoxy)-1,2,3-triazolo[1,5-α]pyrimidine;

6-cyclobutyl-3-(2-fluorophenyl)-5-(1-methyl-1H-1,2,4-triazol-3-ylmethoxy)-1,2,3-triazolo[1,5-α]pyrimidine;

6-cyclobutyl-5-(2-ethyl-2H-1,2,4-triazol-3-ylmethoxy)-3-(2-fluorophenyl)-1,2,3-triazolo[1,5-α]pyrimidine;

3-(2-fluorophenyl)-5-(1-methyl-1H-1,2,4-triazol-3-ylmethoxy)-6-phenyl-1,2,3-triazolo[1,5-α]pyrimidine;

5-(2-ethyl-2H-1,2,4-triazol-3-ylmethoxy)-3-(2-fluorophenyl)-6-phenyl-1,2,3-triazolo[1,5-α]pyrimidine; and salts thereof.

8. A pharmaceutical composition comprising a compound of formula (I) as defined in claim 1 or a pharmaceutically acceptable salt thereof in association with a pharmaceutically acceptable carrier.

9. A process for the preparation of a compound as claimed in claim 1, which comprises reacting a compound of formula III with a compound of formula IV:

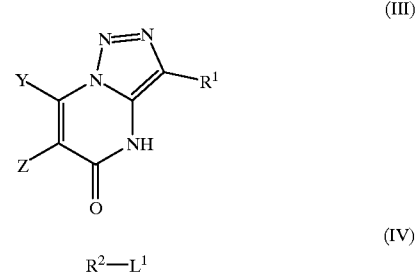

(III)

(IV)

$R^2$—$L^1$ wherein Y, Z, $R^1$, and $R^2$ are as defined in claim 1, and $L^1$ represents a suitable leaving group.

10. A method for the treatment or prevention of anxiety which comprises administering to a patient in need of such treatment an effective amount of a compound of formula I as defined in claim 1 or a pharmaceutically acceptable salt thereof.

* * * * *